United States Patent [19]

Gray et al.

[11] 4,366,330

[45] Dec. 28, 1982

[54] INTERMEDIATES USEFUL IN THE PRODUCTION OF LIQUID CRYSTAL COMPOUNDS

[75] Inventors: George W. Gray; David Lacey, both of Cottingham; John A. Jenner, Wimborne; Martin G. Pellatt, Wimborne, all of England

[73] Assignees: BCH Chemicals Limited; The Secretary of State for Defence in Her Britannic Majesty's Government of the United Kingdom of Great Britain and Northern Ireland, both of England

[21] Appl. No.: 192,556

[22] Filed: Sep. 30, 1980

[30] Foreign Application Priority Data

Oct. 2, 1979 [GB] United Kingdom ............ 7934128

[51] Int. Cl.³ .................................... C07C 39/27
[52] U.S. Cl. ................................ 568/775; 568/743; 568/745; 568/744
[58] Field of Search ............ 568/775, 744, 745, 746, 568/743

[56] References Cited

U.S. PATENT DOCUMENTS 2,086,336 7/1937 Raiziss et al. .................. 568/775
3,510,528 5/1970 Stevick ......................... 568/775
4,122,288 10/1978 Christensen et al. ............ 568/775

OTHER PUBLICATIONS

Suter et al., "J. Amer. Chem. Soc.", vol. 61, pp. 161–165, (1939).
Joshi et al., "J. Indian Chem. Soc.", vol. 37, pp. 687–689, (1960).
Joshi et al., "J. Indian Chem. Soc.", vol. 37, No. 11, pp. 685–686, (1960).
Joshi et al., "J. Indian Chem. Soc.", vol. 38, pp. 768–779, (1961).

*Primary Examiner*—Werren B. Lone
*Attorney, Agent, or Firm*—Stevens, Davis, Miller & Mosher

[57] ABSTRACT

An intermediate useful in the production of liquid crystal esters has a molecular structure

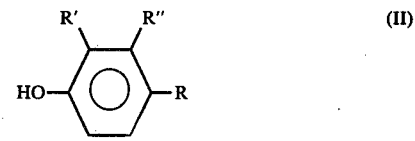

in which of the groups R' and R" one is fluorine and the other is hydrogen, and in which R is an alkyl group having more than one carbon atom, an aryl substituted alkyl group or a cyclohexyl substituted alkyl group.

These compounds may be prepared from the corresponding alkoxy compounds

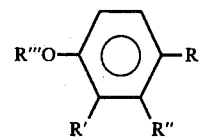

where R''' is a protective alkyl group such as methyl.

These compounds may be used in the production of liquid crystal esters by a conventional esterification with carboxylic acids, or acid derivative, eg chloride, eg containing the radical

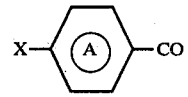

where X is an alkyl group and

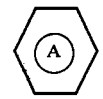

is a benzene or cyclohexane ring.

12 Claims, No Drawings

INTERMEDIATES USEFUL IN THE PRODUCTION OF LIQUID CRYSTAL COMPOUNDS

The present invention relates to intermediates useful in the production of liquid crystal compounds.

The use of liquid crystal materials to exhibit electro-optic effects in display devices such as digital calculators or watches is now well-known. One of the parameters of a liquid crystal material which is important in relation to electro-optical operation is the dielectric anisotropy ($\Delta\epsilon$) of the material. This is the difference, for a given frequency and temperature, between the average dielectric constant measured parallel ($\epsilon_{\parallel}$) to the long axis of the molecules of the material, eg when aligned together, less the average dielectric constant measured perpendicular ($\epsilon_{\perp}$) to the long axis of the molecules.

The sign and magnitude of the dielectric anisotropy of a given liquid crystal material is one of the major parameters which determine the kinds of electro-optic devices in which that material may be used.

For example, materials having a large positive dielectric anisotropy, herein referred to as 'strongly positive' materials may be used in known twisted nematic effect devices. For example mixtures of 4-alkyl-or-alkoxy-4'-cyanobiphenyls and a 4"-alkyl-or-alkoxy-cyano-p-terphenyl have achieved considerable commercial success in such applications.

Materials having a large negative dielectric anisotropy may for example (depending on other properties such as resistivity) be used in known dynamic scattering effect and cholesteric memory effect devices.

Materials having a small positive or negative dielectric anisotropy, herein referred to as 'weakly' positive or negative materials as appropriate, may be mixed with either strongly positive materials or strongly negative materials to modify the dielectric anisotropy.

For example weakly positive or negative materials are useful for blending with strongly positive materials for multiplexed twisted nematic effect devices. Furthermore, they may also be blended with strongly negative materials to form suitable mixtures for positive contrast guest-host devices.

It is the purpose of the present invention (in one aspect) to facilitate the synthesis of liquid crystal compounds which are either weakly positive or weakly negative materials (preferably negative).

The sign and magnitude of the dielectric anisotropy of a liquid crystal material is determined (inter alia) by the resultant dipole moment of the molecules of the material which in turn is determined by the various substituents within the molecule. Positive materials have a resultant dipole moment along the long axis of the molecule, whilst negative materials possess a resultant dipole moment at right angles to the long axis of the molecule.

The known group of liquid crystals based on the ester structure (I) as given below in which the six membered ring A may be aromatic or saturated and in which both rings carry appropriate substituents in the 4 and 4' positions,

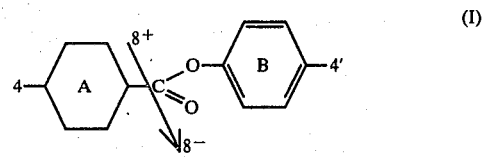

may show positive or negative dielectric anisotropy according to the degree of interactions of the 4 and 4' substituents with the dipole produced by the central carbonyl grouping. Incorporation of a powerfully electronegative grouping in the 4' position, such as a cyano-grouping, for example, induces a resultant dipole along the axis of the molecule and hence confers positive dielectric anisotropy. On the other hand, if the 4 and 4' substituents are but weakly electron attracting or releasing, the direction of the resultant dipole moment is determined by the carbonyl group, and the component of its dipole at right angles to the long axis of the molecule may confer negative dielectric anisotropy.

Ester structures may be substituted in such a way that additional dipoles are introduced into the molecule to reinforce the component of the carbonyl dipole at right angles to the molecular axis, with the object of at least slightly enhancing the negative dielectric anisotropy or diminishing the positive dielectric anisotropy of the molecule.

It is apparent superficially that such an objective may be achieved by introducing polar groups into the 2', 3', 5' and 6' positions of ring B. However it is well-known that the introduction of groupings in these positions may, because of their steric influence, diminish the lateral attractions between the molecules which produce liquid crystal properties. Such substituted molecules may not show liquid crystal properties at all, or may show only monotropic phases.

The discovery has now been made, which is further described in our co-pending UK Patent Application, that in general terms the substitution of fluorine atoms in the 2' or 3' positions of ester structure (I) slightly enhances the negative dielectric anisotropy or diminishes the positive dielectric anisotropy of the molecule by the mechanism described above, but, more importantly, still retains liquid crystal properties in the molecules. The present invention provides the intermediate phenols and methods of manufacturing them which enable such fluoro-substituted esters to be prepared.

According to the present invention in a first aspect, an intermediate useful in the production of liquid crystal esters has a molecular structure:

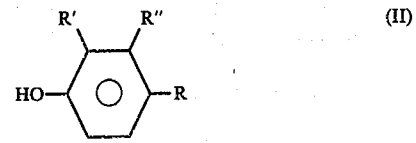

in which R' represents a hydrogen or fluorine atom, R" represents fluorine when R'=H or hydrogen when R'=F, and R represents an alkyl grouping with more than 1 carbon atom which may be a straight chain alkyl grouping, or a branched alkyl group, which may contain an optically active carbon atom, or where R may represent an aralkyl or cyclohexyl substituted alkyl grouping.

According to the present invention in a second aspect there is provided the use of an intermediate of structure (II) in the production of a liquid crystal ester, including reacting the intermediate with the carboxylic acid of a cycloalkyl or aryl compound.

For example a method of producing a liquid crystal ester having a structure

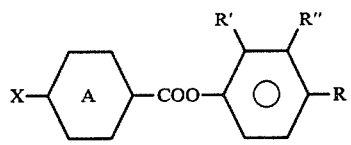
(III)

involves an esterification of a phenol having structure (II) above together with an acid or acid derivative containing the group

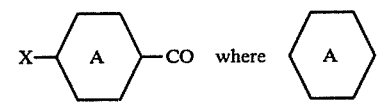 where

is a benzene or cyclohexane ring and X is an alkyl group where

is a benzene or cyclohexane ring or X is an alkoxy, alkanoyloxy or alkoxy carbonyloxy group where

is a benzene ring, R, R' and R" being as defined above. (When A is a cyclohexane ring the stereochemistry is such that the 1,4 substituents are trans.)

The esters of structure (III) are further described in copending U.K. patent application No. 7934127, although examples of the use according to the second aspect are given below.

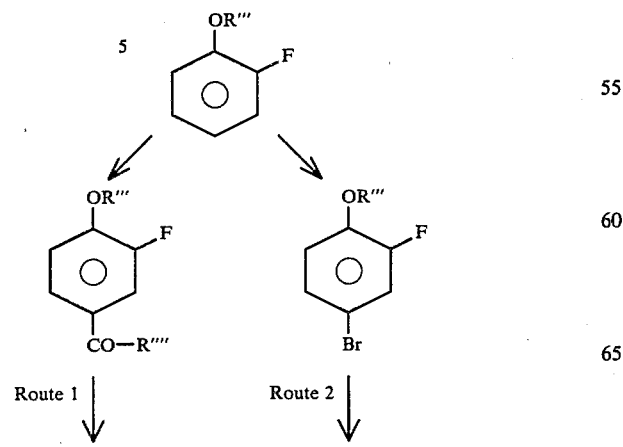

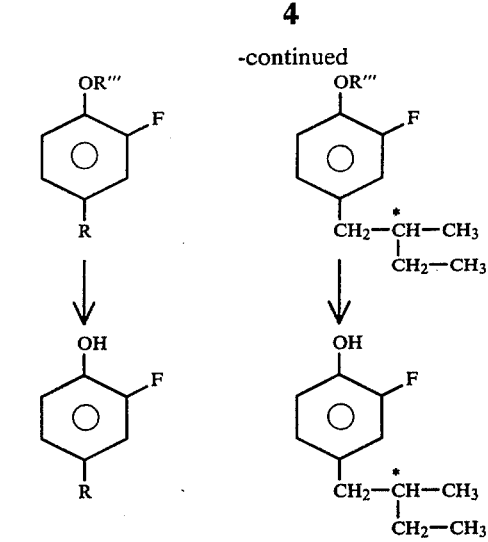

where R is as defined above and R''' is a protective alkyl group such as methyl.

Typically, but not restrictively, 3-fluoro-4-substituted-phenols embodying structure (II) above may be synthesised by Route 3 as follows:

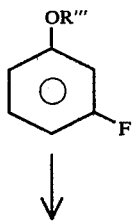

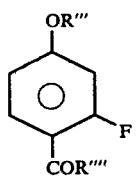

Route 3

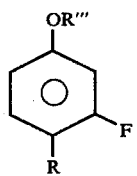

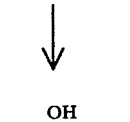

Where R is as defined above. R''' is a protective alkyl grouping such as methyl.

Examples of the preparation and properties of phenols having structure (II) as defined above will now be given.

EXAMPLE 1

A 3-necked flask was fitted with stirrer, thermometer, dropping funnel and calcium chloride drying tube, and immersed in an ice-salt bath. Anhydrous aluminium chloride (106 g) and dichloromethane (250 ml) were placed in the flask and stirred vigorously whilst a solution of valeryl chloride (95.5 g) 2-fluoroanisole (100 g) in dichloromethane (250 ml) was added at a rate sufficiently slow to ensure that the temperature of the reaction did not rise above 15° (approx 1 hour). When the addition was complete, the reaction was stirred overnight, the temperature being allowed to rise to room temperature.

The reaction was poured onto ice (1.5 kg) with vigorous stirring, and stirred for 30 minutes. The organic layer was separated off, and the aqueous layer extracted with dichloromethane (150 ml). The combined organic layers were washed with water (150 ml) dried ($Na_2SO_4$), filtered and the solvent removed by distillation, finally under slight vacuum. The crude 4-valeryl-2-fluoroanisole a slightly yellow low-melting solid, was used directly without further purification.

A small quantity was distilled, b.pt. 100°–102° C. at 0.15 mm. NMR $\tau$9.0 (m,$CH_3$—$CH_2$), 8.5 (m,$CH_2$—$CH_2$), 7.2 (t,$CH_2$—CO), 6.1 (s, $OCH_3$), 2,2–3,3 (m, aromatic H).

tlc 1 spot ($CH_2Cl_2$)
glc 99.7% pure

4-Valeryl-2-fluoroanisole (from 100 g 2-fluoroanisole), hydrazine hydrate (102 ml), potassium hydroxide (52.5 g) and 1:2-dihydroxyethane (1.01) were placed in a flask equipped with stirrer, double surface condenser and thermometer, and boiled under reflux for 1½ hours at 150° C. The apparatus was arranged for distillation, and liquid was distilled until the temperature in the flask reached 190° C. The distillate was retained. The apparatus was arranged for reflux, which was continued for 12 hours, after which the reaction was allowed to cool.

The distillate was extracted with petroleum spirit (b.p 40°–60°, 2×150 ml). The cooled reaction was poured into cold water (2 liters) and extracted with petrol (1×500 ml, 2×150 ml). The five petrol extracts were combined, washed with water (250 ml) and the petrol removed by distillation. The light yellow oily residue (60 g) was distilled under high vacuum through a small Vigreux column (6", B24), and a small forerun was discarded. 4-Pentyl-2-fluoroanisole, a colourless oil, had b.pt 72°–75° C. at 0.2 mm.

Yield 49 g (31% theory)
tlc 1 spot (1:1 dichloromethane:petrol)

4-Pentyl-2-fluoroanisole (49 g), 47% hydrobromic acid (196 ml) and 45% hydrogen bromide in acetic acid (294 ml) were boiled together under reflux for 18 hours. The hydrogen bromide that was evolved was absorbed in water with a scrubber.

The reaction was cooled to 15° C., poured into water (1.01) and extracted with dichloromethane (3×250 ml). The combined extracts were washed with water (2×500 ml), dried ($Na_2SO_4$, 30 min), filtered and the solvent removed by distillation. The dark oily residue (46 g) was distilled under high vacuum through a 6" Vigreux column. 4-Pentyl-2-fluorophenol, a colourless oil, was collected at b.pt 101°–103° C. at 0.65 mm, after discarding a small forerun.

Yield 33.2 g (73% theory)
Analysis:
  glc 98.5% pure
  tlc 1 spot ($CH_2Cl_2$)

The 4-alkyl-2-fluorophenols listed in Table 1 were prepared in a similar manner using the appropriate acid chloride at the first stage of the synthesis.

TABLE 1

4-n-Alkyl-2-fluorophenols 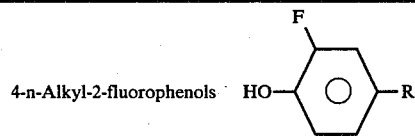

| R | Boiling Point | Empirical formula | Analysis found C | H | Analysis required C | H |
|---|---|---|---|---|---|---|
| $C_3H_7$ | 54–55° C. at 0.3mm | $C_9H_{11}OF$ | 69.7% | 7.4% | 70.1% | 7.2% |
| $C_4H_9$ | 66–67° C. at 0.4mm | $C_{10}H_{13}OF$ | 71.3% | 8.5% | 71.4% | 7.8% |
| $C_5H_{11}$ | 68–69° C. at 0.3mm | $C_{11}H_{15}OF$ | 72.5% | 8.7% | 72.5% | 8.3% |
| $C_6H_{13}$ | 80–82° C. at 0.2mm | $C_{12}H_{17}OF$ | 73.4% | 9.5% | 73.4% | 8.7% |
| $C_7H_{15}$ | 101–103° C. at 0.65mm | $C_{13}H_{19}OF$ | 74.4% | 9.5% | 74.3% | 9.1% |
| $C_8H_{17}$ | 125–128° C. at 0.9mm | $C_{14}H_{21}OF$ | 75.4% | 10.2% | 75.0% | 9.4% |
| $C_9H_{19}$ | 124° C. at 0.6mm | $C_{15}H_{23}OF$ | 75.4% | 10.3% | 75.6% | 9.7% |
| $C_{10}H_{21}$ | 106° C. at 0.5mm | $C_{16}H_{25}OF$ | 76.0% | 10.3% | 76.2% | 10.0% |
| $C_{11}H_{23}$ | 135–136° C. at 0.7mm | $C_{17}H_{27}OF$ | — | — | — | — |

Analogous compounds in which R=$C_2H_5$, n-$C_8H_{17}$, n-$C_9H_{19}$ and n-$C_{10}H_{21}$ may also be made in a similar way.

EXAMPLE 2

A solution of bromine (48 g) in chloroform (100 ml) was added during 10 minutes to a well-stirred solution of 2-fluoroanisole (37.8 g) in chloroform (100 ml). The mixture became warm and hydrogen bromide fumes were evolved. The solution was boiled under reflux with stirring until the colour of the bromine faded (approximately 2½ hours). The chloroform was recovered by distillation and the light yellow oily residue was distilled under high vacuum through a small Vigreux column (6 in, B24). 4-Bromo-2-fluoroanisole, a colourless oil, had b.pt 60°–61° C. at 0.5 mm. Yield 45.2 g (82% theory).

A 500 ml flask was equipped with stirrer, dropping funnel and double surface condenser with calcium chloride guard tubes to maintain anhydrous conditions. The flask was placed in an empty water bath and charged with magnesium turnings (3.9 g) and sodium-dried ether (45 ml). A small volume of a solution of 4-bromo-2- fluoroanisole (31.2 g) in sodium-dried ether (60 ml) was added to the magnesium, and a single crystal of iodine, followed by a few drops of 1,2-dibromoethane, was added to initiate the reaction. Once the reaction had begun, the remaining solution of 4-bromo-2-fluoroanisole was added dropwise with stirring so as to maintain the reaction at a steady rate. When the addition was complete, reflux was maintained for a further hour with stirring. The Grignard solution was then cooled in an ice-bath and cuprous chloride (0.9 g) and sodium-dried ether (25 ml) were added, followed immediately by a solution of (+)-2-methylbutylbenzene sulphonate (72 g) in sodium-dried ether (60 ml) at such a rate that the reaction maintained gentle reflux. When the addition was complete the reaction was stirred at room temperature for 24 hours, and then boiled under reflux for a further 16 hours.

The reaction mixture was cooled, and then poured into 10% aqueous hydrochloric acid (225 ml) at 0° C., and stirred for 1 hour. The ether layer was recovered, and the aqueous layer was extracted with ether (3×100 ml). The ether layer and extracts were combined, filtered through a small Hyflo pad, washed with water (3×100 ml), dried ($Na_2SO_4$), filtered and the solvent removed by distillation.

The oily residue was distilled on a steambath under high vacuum (0.1 mm) into a cold trap cooled with dry ice, and distillation was continued until condensation of the colourless product ceased. The major part of the product distilled at 60°–80° C. at 0.1 mm. The distillate was redistilled under high vacuum through a small Vigreux column (6 in, B24) and 4-(2-methylbutyl)-2-fluoroanisole was collected at 66°–67° C. at 0.15 mm, after discarding a small forerun. Yield 13.4 g (45% theory), tlc 1 spot ($CH_2Cl_2$).

4-(2-Methylbutyl)-2-fluoroanisole (12.4 g), 47% hydrobromic acid (49.6 ml) and 45% hydrogen bromide in acetic acid (74.4 ml) were boiled together under reflux for 18 hours. The hydrogen bromide evolved was absorbed in water with a scrubber.

The reaction was cooled to 15° C., poured into water (250 ml) and extracted with dichloromethane (3×75 ml). The combined extracts were washed with water (2×150 ml), dried ($Na_2SO_4$, 30 min), filtered and the solvent removed by distillation. The dark oily residue was distilled under high vacuum through a small Vigreux column (6 in, B24). (+)-4-(2-methylbutyl)-2-fluorophenol, a colourless oil, was collected at b.pt 69°–70° C. at 0.7 mm, after discarding a small forerun. Yield 7.0 g (61% theory), glc 98.8% pure, tlc 1 spot ($CH_2Cl_2$) [α] 20°/D+8.0° (c=4.85 in chloroform).

(+)-4-(2-methylbutyl)-3-fluorophenol may be made in an analogous way.

EXAMPLE 3

3-Fluoroanisole (20 g), valeryl chloride (19.1 g) and aluminium chloride (21.3 g) were reacted together in dichloromethane (100 ml) as described in Example 1. The product, a yellow oil, was distilled under high vacuum through a small Vigreux column (6 in, B24) and four fractions were taken:

| Fraction 1 | b.pt | 80–90° C. | at | 0.25 mm |
| Fraction 2 | b.pt | 90–100° C. | at | 0.2 mm |
| Fraction 3 | b.pt | 100–123° C. | at | 0.1 mm |
| Fraction 4 | b.pt | 123° C. rising | at | 0.1 mm |

Fractions 2 and 3, analysed by glc, consisted mainly of the required isomer, whilst fraction 1 contained a high proportion of 6-valeryl-3-fluoroanisole. Fractions 1 and 4 were combined and chromatographed on a column of silica gel (70 g). Fractions containing pure 4-valeryl-3-fluoroanisole, eluted with 2:1 petroleum spirit-dichloromethane, were combined. Fractions 2 and 3 were combined and treated similarly (silica gel, 80 g). The fractions containing 4-valeryl-3-fluoroanisole were combined and distilled to dryness, finally under vacuum.

The product, a colourless oil, did not crystallise on standing. Yield 14 g (42% theory), tlc ($CH_2Cl_2$) 1 spot, glc 97.7% pure, NMR τ8.9 (t, $CH_3$—$CH_2$), 8.5 (m, $CH_2$—$CH_2$), 7.1 (m, $CH_2$—CO), 6.2 (s, $CH_3O$), 2.0–3.6 (m, aromatic H).

4-Valeryl-3-fluoroanisole (14.1 g), hydrazine hydrate (8.6 ml) potassium hydroxide (4.4 g) and 1:1 dihydroxyethane (84 ml) were reacted together as described in Example 1. 4-Pentyl-3-fluoroanisole was isolated as a colourless oil b.pt 77° C. at 0.1 mm. The product showed 1 spot only on tlc using dichloromethanepetrol (1:1) as solvent.

4-Pentyl-3-fluoroanisole (2.2 g), 47% hydrobromic acid (9.0 ml) and 45% hydrogen bromide in acetic acid (13.25 ml) were reacted together as described in Example 1. The crude product was chromatographed on a column of silica gel (50 g) and fractions containing pure 4-pentyl-3-fluorophenol, eluted with 1:1 dichloromethane:petrol were combined and distilled to dryness to leave a light yellow oil. Yield 1.4 g (69% theory), glc 96.6% pure, tlc 1 spot ($CH_2Cl_2$).

The 4-alkylphenols described in Table 2 were prepared by the method above using the appropriate acid chloride.

TABLE 2

| R | Empirical formula | 4-n-Alkyl-3-flourophenols | | | |
|---|---|---|---|---|---|
| | | Analysis found | | Analysis required | |
| | | C | H | C | H |
| n-$C_3H_7$ | $C_9H_{11}OF$ | 69.1% | 7.8% | 70.1% | 7.2% |
| n-$C_4H_9$ | $C_{10}H_{13}OF$ | 70.9% | 8.5% | 71.4% | 7.8% |
| n-$C_5H_{11}$ | $C_{11}H_{15}OF$ | 71.7% | 8.7% | 72.5% | 8.3% |

Analogous compounds in which R=$C_2H_5$, n-$C_6H_{13}$, n-$C_7H_{15}$, n-$C_8H_{17}$, n-$C_9H_{19}$ and n-$C_{10}H_{21}$ may also be made in a similar way.

An example of the use of the phenols embodying the invention will now be given. The route is as follows:

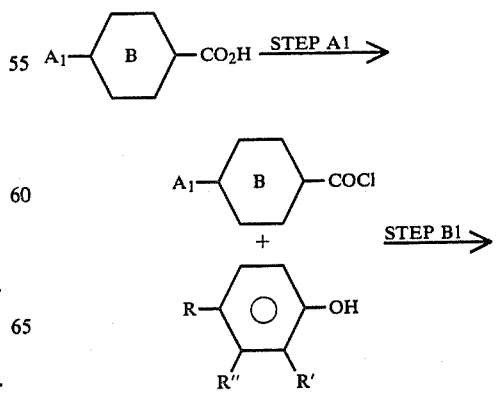

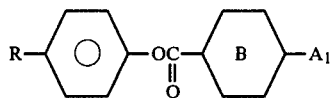

where B is a trans-cyclohexane ring, A₁ being n-alkyl, or where B is a phenyl ring, A₁ being n-alkyl or n-alkoxy.

The preparation of 4-n-pentyl 1-2-fluorophenyl 4'-n-butyloxybenzoate typifies the esterification procedure used to prepare these esters. This compound has been produced as follows.

STEP A1

4-n-butyloxybenzoic acid (0.0082 M) was converted into the acid chloride using freshly distilled thionyl chloride (15 cm³).

STEP B1

To a cold, stirred solution of the acid chloride prepared in Step A1 in dry dichloromethane (15 cm³) was added, dropwise, a cold solution of 4-n-pentyl-2-fluorophenol (0.0082 M) in dry dichloromethane (15 cm³) and triethylamine (10 cm³), keeping the temperature below 10° C. When the addition had been completed, the reaction mixture was heated under reflux, with stirring for 3 h.

After cooling, the dichloromethane and triethylamine were distilled off, under reduced pressure, and ether was then added to the residue. The undissolved triethylamine hydrochloride was filtered off and the ethereal extract washed successively with 10% hydrochloric acid, 5% aqueous sodium carbonate, and water and finally dried (Na₂SO₄).

The crude residual ester was then column chromatographed on silica gel, eluting with chloroform (2): light petroleum (bp 60°–80°) (1). Several recrystallisations from ethanol gave the 2-fluoro-4-n-pentylphenyl 4'-n-butyloxybenzoate as a colourless crystalline solid, 1.9 g (61% yield).

Esters such as 2-fluoro-4-b-pentylphenyl 4'-n-butylbenzoate and 2-fluoro-4-n-pentylphenyl trans-4'-n-butylcyclohexylcarboxylate were purified by the above chromatographic procedure and then further purified by distillation under reduced pressure, to afford the esters as colourless liquids. The cyclohexane ester mentioned above was further recrystallised from ethanol, using solid carbon dioxide, to give this ester as a colourless crystalline solid, which rapidly melted at room temperature.

Spectroscopic analysis, thin layer chromatography, and gas liquid chromatography were carried out on all the esters prepared by the method to verify their structure and/or purity.

We claim:

1. A phenol which is adapted for reaction with an aryl or cycloalkyl carboxylic acid to produce an ester having a dielectric anistropy which adapts it for a liquid crystal material for electro-optical display devices and having the formula

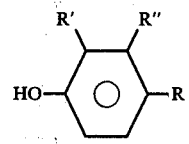

wherein one of R' and R" is fluorine and the other is hydrogen and R is an alkyl group having from 3 to 11 carbon atoms, an aryl substituted alkyl group, or a cyclohexyl substituted alkyl group.

2. The phenol of claim 1 wherein R' is fluorine and R" is hydrogen.

3. The phenol of claim 1 wherein R' is hydrogen and R" is fluorine.

4. The phenol of claim 1 wherein R is n-$C_3H_7$.

5. The phenol of claim 1 wherein R is n-$C_4H_9$.

6. The phenol of claim 1 wherein R is n-$C_5H_{11}$.

7. The phenol of claim 1 wherein R is n-$C_6H_{13}$.

8. The phenol of claim 1 wherein R is n-$C_7H_{15}$.

9. The phenol of claim 1 wherein R is (+)-2-methylbutyl.

10. The phenol of claim 3 wherein R is n-$C_3H_7$.

11. The phenol of claim 3 wherein R is n-$C_4H_9$.

12. The phenol of claim 3 wherein R is n-$C_5H_{11}$.

* * * * *

UNITED STATES PATENT AND TRADEMARK OFFICE
CERTIFICATE OF CORRECTION

PATENT NO. : 4,366,330

DATED : December 28, 1982

INVENTOR(S) : GRAY, et al.

It is certified that error appears in the above-identified patent and that said Letters Patent is hereby corrected as shown below:

On the title page

[73] "BCH Chemicals Limited and The Secretary of State for Defence in Her Britannic Majesty's Government of the United Kingdom of Great Britain and Northern Ireland" should be

[73] -- BDH Chemicals Limited and The Secretary of State for Defence in Her Britannic Majesty's Government of the United Kingdom of Great Britain and Northern Ireland--.

Signed and Sealed this

Twelfth Day of February 1985

[SEAL]

Attest:

DONALD J. QUIGG

Attesting Officer     Acting Commissioner of Patents and Trademarks